United States Patent [19]
Parris

[11] Patent Number: 5,653,862
[45] Date of Patent: Aug. 5, 1997

[54] BIOCHEMICAL SENSOR DEVICE AND METHOD

[75] Inventor: Norman Alfred Parris, Hockessin, Del.

[73] Assignee: Dade Chemistry Systems Inc., Newark, Del.

[21] Appl. No.: 632,202

[22] Filed: Apr. 15, 1996

[51] Int. Cl.⁶ .................................................. G01N 27/26
[52] U.S. Cl. ........................ 205/777.5; 204/403; 204/409
[58] Field of Search ............................... 435/817, 12, 14, 435/25; 204/403, 409; 205/777.5

[56] References Cited

U.S. PATENT DOCUMENTS

| 4,452,682 | 6/1984 | Takata et al. | 204/403 |
| 4,759,828 | 7/1988 | Young et al. | 204/1 |
| 5,063,081 | 11/1991 | Cozzette et al. | 427/2 |

FOREIGN PATENT DOCUMENTS 2063479  6/1981  United Kingdom.

OTHER PUBLICATIONS

Murachi et al. (abstract of Biotechnol. Appl. Biochem.; "Use of a Bioreactor Consisting of Sequentially Aligned L-glutamate Dehydrogenase and L-glutamate oxidase for the Determination of Ammonia by Chemiluminescence"; (1987), 9(4), 303–9) no month available 1987.

Rui et al. (Biosci. Biotech. Biochem.; "Multifunctional Flow-Injection Biosensor for the Simultaneous Measurement of Creatine", Glucose, and Urea; 57(2), 191–194,1993 no month available 1993.

*Primary Examiner*—Kathryn L. Gorgos
*Assistant Examiner*—Alex Noguerola
*Attorney, Agent, or Firm*—Leland K. Jordan

[57] ABSTRACT

Degradation of multielectrochemical sensors in a common flow stream is averted by positioning any sensors having as its associated enzyme an oxidoreductase enzyme capable of producing, as a result interaction with its respective substrate, an oxidizing agent downstream of the other enzyme sensors not having such oxidoreductase enzyme.

4 Claims, 3 Drawing Sheets

BIOCHEMICAL SENSOR DEVICE AND METHOD

This invention relates to enzyme-based bioanalytical measurement devices (biosensors) and their use in chemical or clinical analysis. More specifically, this invention provides a means to extend the useful life of such biosensors.

BACKGROUND OF THE INVENTION

Since the pioneering work of Updike and Hicks, Nature (London), Vol. 214 (1971) 986, there has been much effort devoted to creating bioanalytical measurement devices by immobilizing an enzyme in, on, or around a measurement device thus creating a biosensor. These so called biosensors find wide application to the field of analytical, environmental and clinical chemistry as well as in the practice of medicine. The principal function of the enzyme(s) in a biosensor is to catalyze the conversion, with a high degree of specificity, of a substance, whose concentration or presence is being sought, into a species that may be readily detected with a chemically selective sensor.

One example of such an application is the combination of urease, an enzyme that specifically hydrolyzes urea to ammonium ions, with an ion-selective electrode or sensor that selectively responds to ammonium ions. Such sensor could have a membrane containing the ionophore nonactin. An ammonium selective sensor would not, in the absence of the enzyme, be able to detect or measure urea.

Another widely used biosensor provides the direct measurement of glucose in physiological fluids. Most common glucose biosensors depend on glucose oxidase catalyzing the oxidation of glucose to hydrogen peroxide. In turn, the concentration of hydrogen peroxide is measured using an amperometric electrochemical cell. The magnitude of the current flowing in the cell is linearly related to the concentration of glucose, as described in U.S. Pat. No. 4,759,828 which is hereby incorporated by reference.

Although many articles related to sensor design, fabrication and use can be found in the technic, al and patent literature, it is widely acknowledged that, to date, there have been very few truly practical biosensors. The technical challenges are many. A notable challenge is maintaining the level of biological activity of the enzyme(s) used in the biosensor so that it may be used for multiple applications.

One approach to achieving and maintaining a high level of enzyme activity, involves mixing the sample of interest with a solution/preparation of the enzyme, immediately before and during the time of measurement. Although this approach does not suffer from the complexities of creating a stable, active, immobilized enzyme, it is fraught with the problem of providing a means to continually add the enzyme containing solution. This increases the complexity of an apparatus used for such analyses and significantly more enzyme is consumed compared with the ideal of a stable, active immobilized enzyme in, on or around the measuring sensor.

Techniques of achieving immobilization of an active enzyme are documented in the technical literature. Enzymes are commonly either adsorbed or covalently attached to, or in close proximity to, the measuring sensor or incorporated into a membrane that is positioned between the sample and the measuring device. Conditions are established to allow the product(s) of the enzymatic process to either interact with a selective sensor surface (an ionophoric layer in the case of a potentiometric device) or diffuse through the membrane to the working electrodes (in the case of an amperometric device). Unfortunately, many biosensors based on such approaches often show disappointing performance. Typical problems include slow hydration of the membrane or degradation of the enzyme by components in the sample or calibration fluids (heavy metals, bacteria or proteases—enzymes that destroy proteins).

In clinical applications, membrane based enzyme systems are preferred since samples can, and do, contain numerous unspecified components that can harm the enzyme used in the biosensor. The membrane matrix is selected to be porous to the test substance, any cofactors or reagents needed by the enzyme, and the byproducts of the reaction. Ideally the membrane structure provides an enzyme-friendly environment while acting as a barrier to agents that will harm the enzyme.

Commercial systems that use biosensors are relatively complex. An advanced system design enables a series of calibration fluids or reagents to be passed sequentially over the biosensors in order to maintain enzyme activity and to calibrate the devices. Good analytical performance is achieved only by rigorous maintenance of the protocol or fluid sequence used. This virtually dictates the need for a computer controlled system.

Notwithstanding the aforementioned efforts, it is apparent that enzyme based sensors do not last indefinitely. Since enzymes represent a significant part of the overall cost of reagents, it is desirable to maximize their useful life. Single use sensors are typically cost prohibitive except in the most specialized applications. Moreover, single use devices, by definition, cannot be calibrated with an authentic fluid to verify functionality and then be used to test a sample.

Multiple use of sensors is cost effective provided protocols for removing prior sample components and reaction byproducts are effective. One method employed by commercial manufacturers is to sequence relatively large volumes of flushing and/or calibration fluids past the sensors. To be effective, refreshing and/or calibrating the sensors is necessary throughout the entire life of the system, whether or not testing is in progress. For any reasonable period of unattended use, it follows that the system must accomodate relatively large volumes of fluid reagents. While this is of little concern for analyzers designed for laboratory use, the problem is more acute for portable or hand held analyzers.

An alternative fairly effective method of extending sensor life is to reduce the volume of sample either by reducing the scale of operation or by pre-diluting the sample. The objective in either case is to limit the amount of substrate a given amount of enzyme the sensor must process and to reduce the overall amount of byproducts. Limiting the sample size with or without dilution tends to increase sensor life and some economy of fluids is achieved. However, attempts to reduce the extent of flushing or calibration invariably leads to a shorter sensor life.

Few manufacturers offer systems based on multiple bioanalytical systems capable of sensing multiple analytes. Even here, sensor life problems appear to be limiting this practical utilization of sensors. Notable exceptions are i-STAT, (Princeton, N.J.) who solves the sensor lifetime problem by employing a single use multianalyte disposable device. One of their systems is described in U.S. Pat. No. 5,063,081.

Another multiuse analyzer is described in U.S. Pat. No. 4,452,682 which tests blood gasses, electrolytes and metabolites. The patent describes a sequential system in which the glucose sensor is positioned upstream of the urea sensor. This system does nothing to enhance the lifetime of the sensor. These prior art sequential flow systems position a glucose sensor which generates hydrogen peroxide ($H_2O_2$) upstream of at least some of other metabolite, i.e., biosensors. This tends to shorten the lifetime of these downstream sensors as described.

NOVA Biomedical (Waltham, Mass.) sells multianalyte sensors and relies on relatively large volumes of flush fluids to assure practical use life. Analyzers marketed by the latter manufacturer use a flow channel to sequentially flow samples and calibration fluids past electrolyte sensors, e.g., sodium, potassium and chloride and then past biosensors for creatinine, glucose and urea.

SUMMARY OF THE INVENTION

Many of the dificiencies of the prior art multianalyte biosensors are reduced by the method and device of this invention. This invention provides a method to enhance the uselife of such biosensors connected in series, while lessening the demand for large volumes of flush fluids. The invention is a bioanalytical measurement device for sensing at least two components of a liquid sample, said device comprising a housing having first and second sensor devices, each comprising a biochemical sensor with an associated enzyme and a flow channel that directs liquids sequentially over said first and second sensor devices; said first sensor device uses an oxidoreductase enzyme capable of producing, as a result of interaction with its respective substrate, an oxidizing agent at least some of which may be released into said flow channel, said first sensor device being positioned downstream of said second sensor device, said housing having measuring means connected with each sensor device.

In one embodiment of the invention, the oxidoreductase enzyme is an oxidase enzyme which creates hydrogen peroxide when acting on the substrate. The oxidase enzyme is selected from the group comprising glucose oxidase, xanthine oxidase, sarcosine oxidase, uricase, alcohol oxidase, cholesterol oxidase, lactose oxidase, lactate oxidase, glutamate oxidase, L-amino acid oxidase and D-amino acid oxidase.

This invention also is a method of sensing at least two components of a liquid sample using first and second sensor devices each having an biochemical sensor with an associated enzyme, said first sensor enzyme being an oxidoreductase enzyme capable of yielding, as a result of interaction with its respective substrate, an oxidizing agent, comprising the steps of passing said liquid sample to each of said first and second sensor devices in a first flow direction, positioning said first sensor device downstream of said second sensor device and measuring the electron activity at each of said sensors.

Use of the method and device of this invention permits the use of a plurality of biosensors for multiple analytes without the reduction in biosensor lifetime that normally accompanies such usage.

Practising this invention prevents the oxidizing agent, most commonly hydrogen peroxide, generated as a product of the action of the oxidoreductase enzyme with its substrate, from destroying sensitive and delicate enzymes downstream. A key learning from this invention that has not been recognized in the prior art, is that microscopic quantities of hydrogen peroxide generated within a sensor based on a oxidoreductase enzyme are sufficient to gradually destroy enzymes positioned downstream. Technology leaders in the field have failed to recognize this source of the problem and positioned glucose upstream from the urea electrode in many commercial analyzers. They generally didn't realize the source of problem and thought the concentration too low to matter.

BRIEF DESCRIPTION OF THE DRAWINGS

The invention will be more fully understood from the following detailed description, taken in connection with the accompanying drawings, which form a part of this application to an invention.

DETAILED DESCRIPTION OF THE PREFERRED EMBODIMENT

Figure 1:
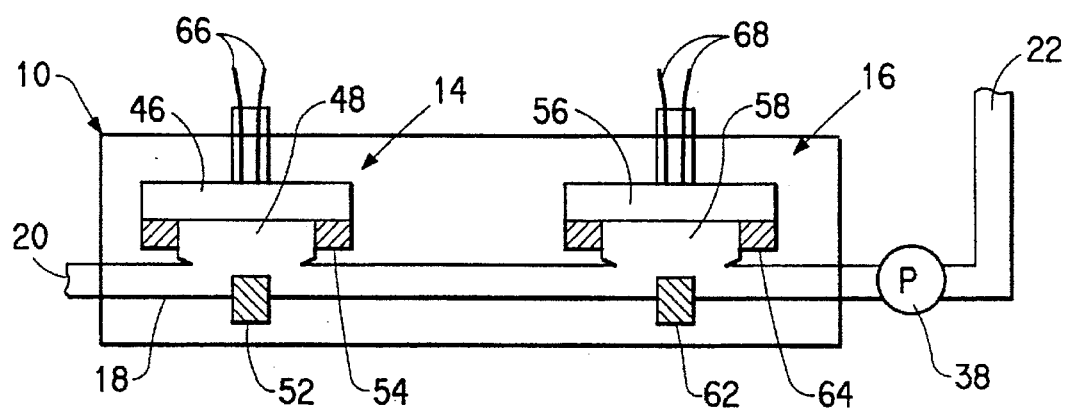
FIG. 1 is a partial sectional view of a biochemical sensor device having at least two sensors serially disposed in a flow channel.

The method of this invention can be used to sense several different analytes using biosensors each having associated enzymes. This method permits the sensing of multiple analytes without serious loss of lifetime of the biosensors and without having to use large volumes of flush fluids.

Definition of Terms in Claims—By "biochemical sensor device" is meant any analytical measurement system that uses a biochemical reaction to generate a detectable species derived from the substance sought for analysis, where the original substance would not otherwise be detected. Examples include, but are not limited to: reactions of enzymes and labelled antibody-antigens conjugates.

By "sensor device" is meant any transducer that can be induced to provide, directly or indirectly, an electrical signal in response to the change in concentration of a chemical species. Examples include potentiometry, amperometric and other electrochemical methods, optical absorbance and fluorescence, bioluminescence, thermal changes, surface acoustic waves and surface plasmon resonance.

By "bioanalytical measurement device" or "biosensor" is meant any sensor that has associated with it an enzyme capable of converting its respective substrate to a measurable species. Enzyme may be provided in solution, adsorbed or covalently attached to, or in, or in close promixity to, or retained in a membrane or gel layer in contact with the active part of the sensor.

By "flow channel" is meant any means for directing the flow or samples, flush or calibration fluids across the active measuring surface of the sensor device, whether by laminar flow or configured in a manner to promote aggressive flushing of the surface, i.e., exploiting turbulent or wall-jet effects.

By "oxidoreductase enzyme" is meant any of the general classes of enzymes capable of either reducing or oxidizing the substrate reversibly or irreversibly depending on the operating conditions.

"Substrate" is taken to have the biochemical meaning, i.e., the starting material for an enzymatic reaction. For example, glucose for glucose oxidase, lipids for lipase, alcohol for alcohol oxidase.

By "oxidase enzyme" is taken to have the biochemical meaning. Generally this general class of enzymes yield hydrogen peroxide during the course of their action on the respective substrate.

By "amperometric measurement" is meant the detection process by which the current required to maintain an applied potential is measured and, in general, is linearly related to analyte concentration via the Ilkovic equation.

The method of this invention will be described in a typical application wherein a first biosensor is designed for the measurement of glucose and the second sensor is designed for the measurement of urea. The glucose biosensor may be any available biosensor that depends on the use of an enzyme which produces hydrogen peroxide as the result of interacting with its respective substrate. One such sensor that may be suitable for such use is that described in U.S. Pat. No. 4,759,828 issued to Nova Biomedical and is incorporated herein by reference. As described hereinabove the glucose biosensor typically results in the generation of hydrogen peroxide which as an oxidizing agent normally deleteriously affects the operation of any downstream electrical chemical sensors.

The second biosensor used in the method of this invention is a urea biosensor such as those described in U.S. Pat. Nos. 5,063,081 or 4,452,682.

In accordance with the method of this invention, a liquid sample is sequentially drawn across the two biosensors each having an associated enzyme. The liquid sample under analysis is first to flowed past the enzyme electrode of the urea biosensor. Such sensor does not generate deleterious hydrogen peroxide. The liquid sample is then flowed past the second biosensor for glucose.

When a liquid sample containing urea enters the urea electrochemical sensor, a portion of the liquid contacts and diffuses into its urea selective membrane 46 (FIG. 1). On contact with the enzyme immobilized within the pores of the membrane, urea is hydrolyzed to ammonium ions and carbon dioxide according to equation:

$$NH_2.CO.NH_2 + H_2O \xrightarrow{urease} 2NH_3 + CO_2$$

At the pH of the sample, ammonia converts to ammonium ions:

$$NH_3 + H^+ \rightarrow NH_4^+$$

The urea (ammonium) measuring sensor responds to the ammonium ions. The measurement is then related to the concentration of urea present in the original sample.

When the liquid sample containing glucose enters the downstream glucose biosensor, a portion of the liquid contacts and diffuses into its glucose selective membrane. On contact with the enzyme immobilized within the pores of membrane and oxygen from the fluids, glucose is oxidized to gluconic acid and hydrogen peroxide according to equation:

$$\text{Beta D-glucose} + O_2 + H_2O \xrightarrow{\text{Glucose Oxidase}} \text{Gluconic Acid} + H_2O_2$$

Hydrogen peroxide diffuses within and from the glucose selective membrane. That hydrogen peroxide that diffuses to the glucose (hydrogen peroxide) sensor is reduced, according to the equation:

$$H_2O_2 \xrightarrow{-2e^-} O_2 + 2H^+$$

Other hydrogen peroxide appears to diffuse into the flow channel where, depending on the fluid sequences, it will be dram downstream and away from any enzymes that would be destructively sensitive to hydrogen peroxide.

Biochemical Sensor Device

The device which can be used to perform the above method and which is constructed in accordance with this invention, is best seen in FIG. 1 and includes a housing 10 which incorporates a flow channel 18 having an inlet 20 and an outlet 22. Liquid is drawn through the flow channel 18. A peristaltic pump 38 or other suitable pumping device connected to outlet 22. Two biosensors, a urea measuring sensor 14 and a glucose measuring sensor 16, are constructed within the housing in an otherwise conventional manner, such as using the teachings of the patents referred to hereinabove. In accordance with this invention the glucose measuring sensor 16 is positioned downstream in the flow channel of the urea measuring sensor 14. The urea measuring sensor 14 includes a urea selective membrane 46 covering a flowthrough chamber 48 constructed using a sealing gasket 54 to have the flow channel 18 flow directed through the chamber 48 using a flow deflector 52. Liquid flow through the flow channel 18 is deflected by a flow deflector 52 to ensure adequate mixing and washout of the measuring chamber 48/50 before and after each measurement. The respective electrodes 66 are connected to a suitable measuring type which may be a potentiometric type.

In a similar manner, the glucose measuring sensor 16, which is positioned as noted downstream from the urea measuring sensor 14, has a glucose selective membrane 56 covering a flow through chamber 58 constructed using a sealing gasket 64 to permit the flow channel 18 to flow through the chamber 58 using a flow deflector 62. Measuring electrodes 68 are connected to a suitable measuring device (not shown). Liquid flow through the flow channel 18 is deflected by a flow deflector 62 to ensure adequate mixing and washout of the measuring chamber 58 before and after each measurement. The respective electrodes 68 are connected to a suitable measuring device which may be of an amperometric type.

This invention uniquely selects the biosensor position for the glucose sensor, which uses an oxidoreductase enzyme that is capable of producing, as a result of interaction with its respective substrate, an oxidizing agent at least some of which may be released into the flow channel. By thus positioning this biosensor downstream of the other sensors, the degradation of the other sensor does not occur as rapidly as it would with the other sensor downstream of the sensor using the oxidoreductase enzyme. This has been demonstrated by various experiments.

EXAMPLE 1

Results with Glucose Sensor Positioned Upstream Relative to Urea Sensor—A flowchannel of the design described was assembled on a DuPont Dimension AR Clinical Chemistry Analyzer in parallel with the Electrolyte (IMT) Flowcell. This system relied on sequentially drawing either clinical samples, i.e., serum, plasma or diluted urine from a sample cup, or calibration standards from plastic bottles, through the previously described flowcell. A microprocessor was used to control the action of a peristaltic pump and a fluid selector arm to draw the appropriate liquids and/or short air segments (to limit mixing) into the flowchannel.

The pump was programmed to stop segments of liquid either calibrants or samples in the flow channel to ensure contact with the sensors. After sufficient time for enzymes to generate a steady state concentration of product, the concentration of ammonium ions (urea sensor) or hydrogen peroxide (glucose sensor) was measured. The products of the reaction and excess sample were subsequently drawn from the flow channel by the pump.

Calibration fluids were processed similarly. Based on prior experience, it was found necessary, when the system was in a "standby" mode, to activate the pump for a short period to move a small volume of liquid to refresh that liquid in contact with the sensors and to exercise the pump tubing.

Figure 2:
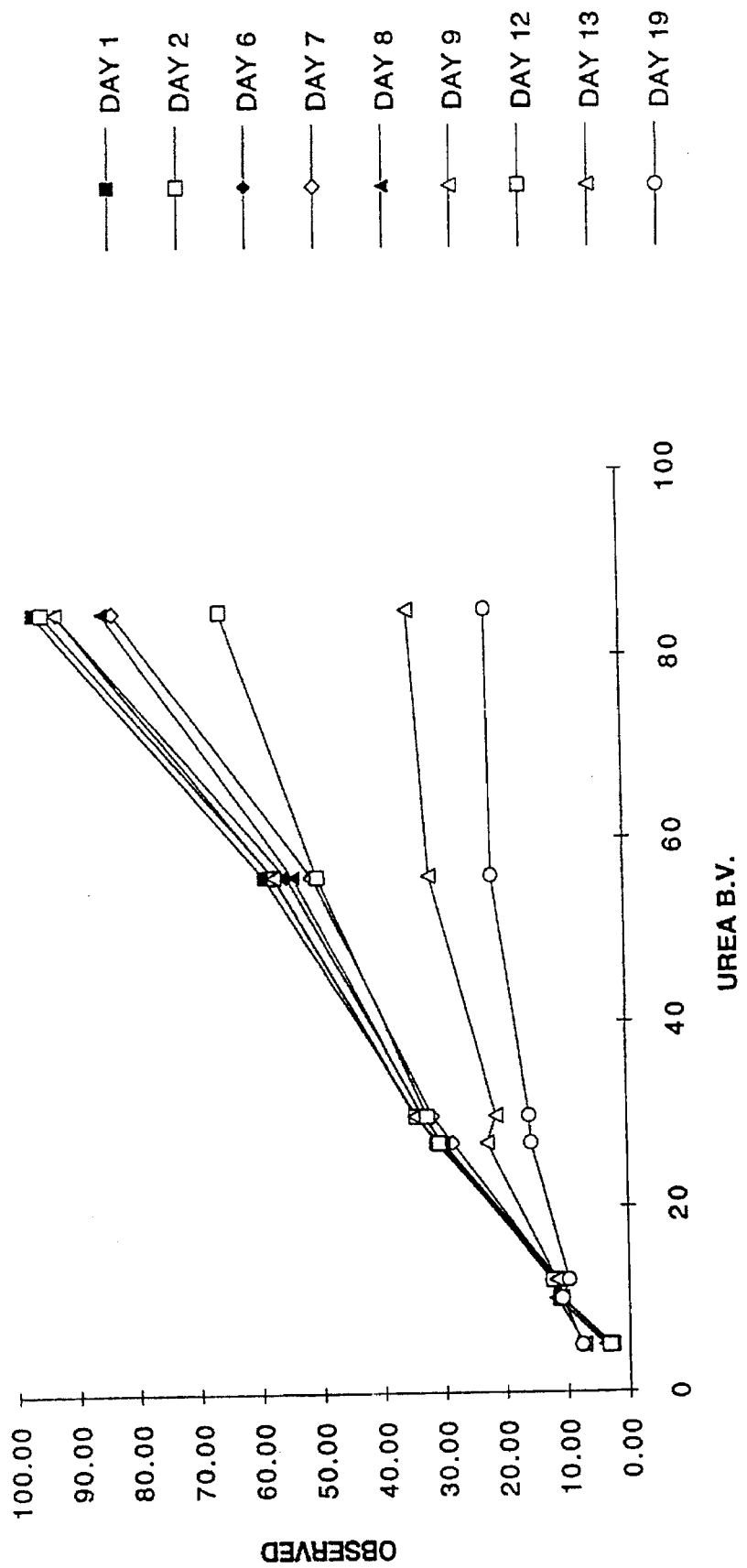
FIG. 2 is the response of the urea sensor in a biochemical sensor device containing a glucose and a urea sensor where the glucose electrode is positioned upstream of the urea sensor as in the prior art.

Each day, for a period extending to 19 days, the analyzer was used to test a series of solutions of known concentration of urea and glucose. Plotting the mean values of these test results against the known value, provided a measure of the useful lifetime of the enzyme urea and glucose selective membrances. FIG. 2 indicates the results from the urea sensor assembly when placed downstream from the glucose sensor assembly.

EXAMPLE 2

Results with Urea Sensor positioned Upstream Relative to Glucose Sensor—The experiment described above was repeated, except that the two sensor assemblies were placed in reverse order, i.e., the glucose sensor was positioned downstream from the urea sensor.

Figure 3:
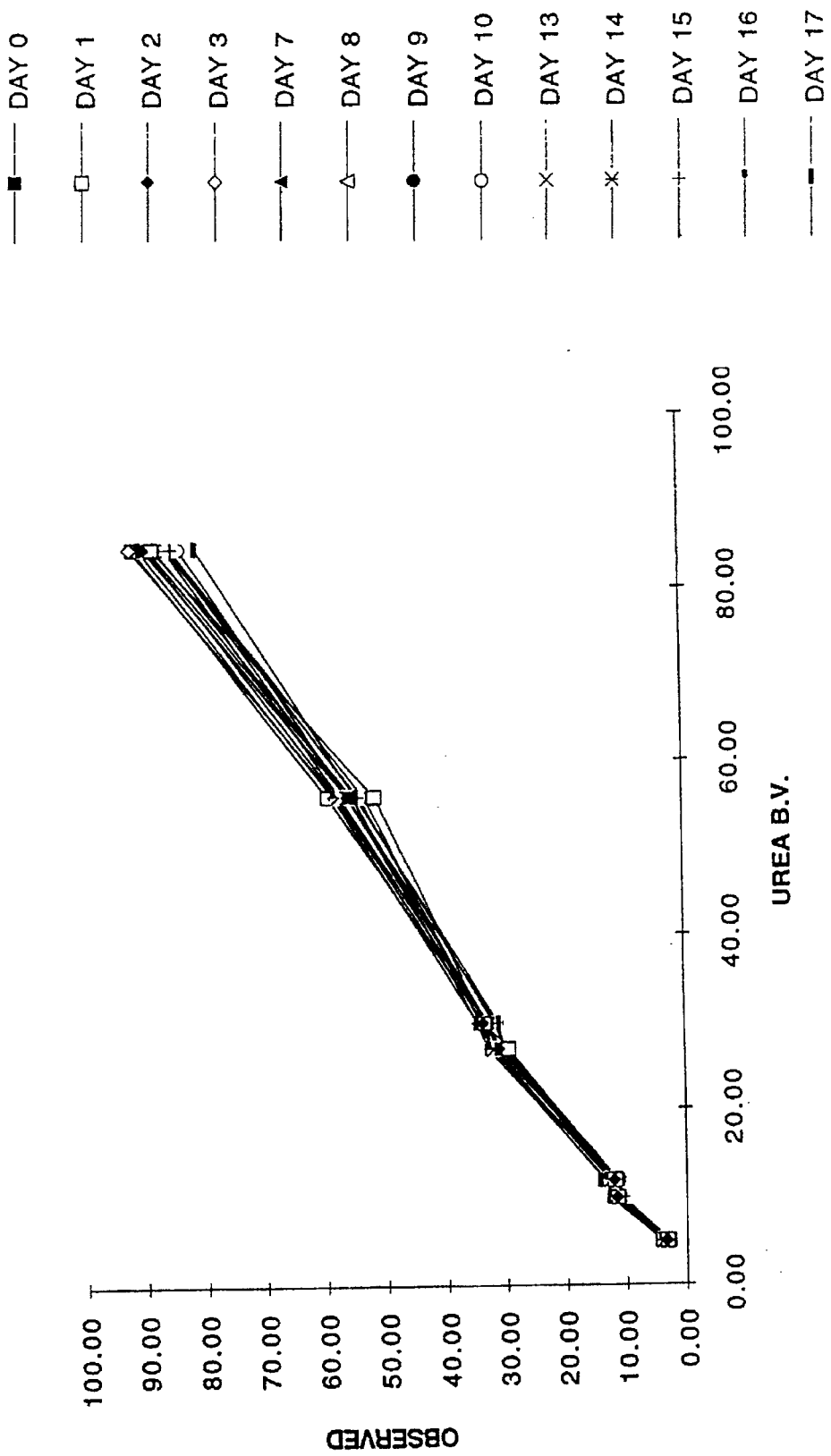
FIG. 3 is the response of the urea sensor in a biochemical sensor device containing a glucose and a urea sensor where the glucose electrode is positioned downstream of the urea sensor in accordance with this invention.

Again, each day, for a period extending to 17 days, the analyzer was used to test a series of solutions of known concentrations of urea and glucose. Plotting the mean values of these test results against the known value, provided a measure of the useful lifetime of the enzyme urea and glucose selective membranes. FIG. 3 indicates the result from the urea sensor assembly when placed downstream from the glucose sensor assembly.

It is clear from these results that the urea sensor experienced a significant reduction in response when the urea sensor was positioned downstream of the sensor using an oxidoreductase enzyme. With the reverse, there was no observable loss of response.

I claim:

1. A bioanalytical measurement device for sensing at least two components of a liquid sample, the device comprising:
    a housing having first and second biochemical sensors, each having an enzyme associated therewith, the housing also having a single flow channel to flow liquid samples over the first and second biochemical sensors in a single direction; and,
    measurement means connected with the first and second biochemical sensors,
    the first biochemical sensor having an oxidase enzyme selected from the group consisting of lactate oxidase, lactose oxidase, and glucose oxidase that produces an oxidizing agent as a result of interaction with its substrate, at least some of oxidizing agent being released into the flow channel,
    the first biochemical sensor positioned in the flow channel downstream of the second biochemical sensor so that oxidizing agents released into the flow channel by the first biochemical sensor do not adversely affect the sensing of the second biochemical sensor.

2. The device of claim 1 wherein the oxidizing agent is hydrogen peroxide.

3. A method for sensing at least two components of a liquid sample using first and second biochemical sensors having enzymes associated therewith, the first biochemical sensor having an oxidase enzyme selected from the group consisting of lactase oxidase, lactose oxidase, and glucose oxidase that produces and oxidizing agent as a result of interaction with its substrate, the method comprising:
    flowing liquid samples within a flow channel over the first and second biochemical sensors in a single direction;
    positioning the first biochemical sensor device in the flow channel downstream of the second biochemical sensor so that oxidizing agents released into the flow channel by the first biochemical sensor do not adversely affect the sensing of the second biochemical sensor; and,
    measuring the chemical activity of each biochemical sensor.

4. The method of claim 3 wherein the oxidizing agent is hydrogen peroxide.

* * * * *

UNITED STATES PATENT AND TRADEMARK OFFICE
CERTIFICATE OF CORRECTION

PATENT NO. : 5,653,862
DATED : August 5, 1997
INVENTOR(S) : Norman Alfred Parris It is certified that error appears in the above-identified patent and that said Letters Patent is hereby corrected as shown below:

Column 1, Line 40: Delete "technic, al" and insert --technical--

Column 4, Line 36: Delete "antigens" and insert --antigen--

Column 5, Line 29: Delete "to"

Column 6, Line 7: Delete "dram" and insert --drawn--

Column 6, Line 67: Delete "flowchannel" and insert --flow channel--

Column 8, Line 28: Delete "lactase" and insert --lactate--

Column 8, Line 29: Delete "and" and insert --an--.

Signed and Sealed this

Eighth Day of September, 1998

Attest:

BRUCE LEHMAN

*Attesting Officer*  *Commissioner of Patents and Trademarks*